(12) United States Patent
Yang et al.

(10) Patent No.: US 9,981,900 B2
(45) Date of Patent: May 29, 2018

(54) METHODS OF METAL OXIDE NANOCRYSTALS PREPARATION

(71) Applicant: CN Innovations, Hong Kong (CN)

(72) Inventors: Dongning Yang, Hong Kong (CN); Ka Ming Ng, Hong Kong (CN); Siu Yeung Chan, Hong Kong (CN)

(73) Assignee: CN Innovations, Hong Kong (CN)

( * ) Notice: Subject to any disclaimer, the term of this patent is extended or adjusted under 35 U.S.C. 154(b) by 88 days.

(21) Appl. No.: 14/251,582

(22) Filed: Apr. 12, 2014

(65) Prior Publication Data

US 2015/0291501 A1      Oct. 15, 2015

(51) Int. Cl.
*C07C 51/41*      (2006.01)
*C07C 53/126*    (2006.01)

(52) U.S. Cl.
CPC .......... *C07C 51/412* (2013.01); *C07C 53/126* (2013.01)

(58) Field of Classification Search
CPC ....... C07C 51/412; C01G 11/00; C01G 15/00; C01G 19/02; C01G 23/047; C01G 29/00; C01G 30/004; C01G 33/00; C01G 37/02; C01G 39/02; C01G 45/02; C01G 49/02; C01G 51/04

See application file for complete search history.

(56) References Cited

U.S. PATENT DOCUMENTS

| | | | | |
|---|---|---|---|---|
| 2,397,767 | A | * | 4/1946 | Taylor .............................. 554/74 |
| 2,528,803 | A | * | 11/1950 | Unkefer ......................... 530/230 |
| 2,573,049 | A | * | 10/1951 | Olson ............................ 530/230 |
| 3,519,571 | A | * | 7/1970 | Szczepanek et al. ..... 252/400.51 |
| 4,235,794 | A | * | 11/1980 | Rieber et al. ................... 554/73 |
| 5,071,800 | A | | 12/1991 | Iwamoto et al. |
| 6,051,166 | A | | 4/2000 | Fujiwara et al. |
| 7,799,312 | B2 | | 9/2010 | Song et al. |

(Continued)

FOREIGN PATENT DOCUMENTS

CN          103205707       *   7/2013

OTHER PUBLICATIONS

CN 103205707, Xiner Huang, Preparation method of novel conductive oxide targets and conductive oxide thin-films, 2013, English abstract, 3 pages.*

(Continued)

*Primary Examiner* — Yate K Cutliff
(74) *Attorney, Agent, or Firm* — Robert Brownstein (57) ABSTRACT

Embodiments relate to methods of metal oxide nanocrystals preparation. In embodiments, a metal-organic precursor may be economically synthesized by reacting a metal with an organic acid. The organic acid may include an aliphatic chain longer than three carbon atoms. The metal may be In, Sn, Al, Ga, Zn, Cd, Sb, Bi, Ge, Mn, Ti, Nb, V, Cr, Mo, Fe, Y, Mg, Co, as well as mixtures thereof. Further processing of the metal-organic precursor (e.g. by pyrolysis, hydrolysis, or alcoholysis) produces metal oxide nanocrystals of desired characteristics. An metal-organic precursor of indium tin oxide (ITO) may be synthesized by reacting indium metal and tin metal with an organic acid having an aliphatic chain longer than three carbon atoms (e.g. stearic acid) at a temperature above 200° C. Further processing of the resulting metal-organic precursor yields ITO nanocrystals of regular shape, uniform size, and average diameter ranging of between about 1-500 nm.

20 Claims, 6 Drawing Sheets

(56) References Cited

U.S. PATENT DOCUMENTS

| | | | |
|---|---|---|---|
| 2006/0211152 A1* | 9/2006 | Peng et al. | 438/3 |
| 2009/0057137 A1* | 3/2009 | Pitts et al. | 204/192.15 |
| 2009/0105493 A1* | 4/2009 | Jang et al. | 556/141 |
| 2011/0006269 A1* | 1/2011 | Petruska et al. | 252/518.1 |
| 2013/0002974 A1* | 1/2013 | Minato et al. | 349/43 |
| 2013/0266800 A1* | 10/2013 | Buonsanti et al. | 428/328 |
| 2014/0220362 A1* | 8/2014 | Milliron et al. | 428/432 |

OTHER PUBLICATIONS

Neves, N. et al., Aluminum doped zinc oxide sputtering targets obtained from nanostructured powders: Processing and application, 2012, Journal of European Ceramic Society, vol. 32.*

Lee J., Lee S., Li G., Petruska M. A., Paine D. C. and Sun S., A facile solution-phase approach to transparent and conducting ITO nanocrystal assemblies, Journal of the American Chemical Society, 2012, 134:p. 13410-13414.

Park J., Joo J., Kwon S. G., Jang Y. and Hyeon T., Synthesis of monodisperse spherical nanocrystals, Angewandte Chemie International Edition, 2007. 46: p. 4630-4660.

Kanehara M., Koike H., Yoshinaga T. and Teranishi T., Indium tin oxide nanoparticles with compositionally tunable surface plasmon resonance frequencies in the near-IR region, Journal of the American Chemical Society, 2009, 131 (49): p. 17736-17737.

* cited by examiner

METHODS OF METAL OXIDE NANOCRYSTALS PREPARATION

BACKGROUND

Metal oxide nanocrystals have attracted extensive interest due to their unique chemical, physical, and electrical properties. Certain materials are known that are both electrically conductive and optically transparent to incident light. One type of this material, a transparent conducting oxide (TCO), is formed by an oxide of one or more metals.

Owing to their optical and electrical properties, TCOs have found use in a variety of applications. One such application is to serve as an electrode of a liquid crystal display (LCD). Other applications utilizing TCOs include solar cells and touch screens.

A commonly-used TCO material comprises indium tin oxide (ITO). ITO nanocrystals have been used to fabricate ITO sputtering targets, which are the main sources to make ITO thin films. Other processes to make ITO films include depositing ITO nanocrystals on the substrate via a solution approach. In general, these two methods to make ITO films call for ITO nanocrystals having regular shapes and uniform sizes with a relatively narrow distribution.

To prepare metal oxide nanocrystals with regular shapes and uniform size, a thermolysis method has been widely used. This method requires large amount of organic solvent and expensive metal-organic precursors for certain kinds of metal oxides. Accordingly, there is a need in the art for novel methods of preparing metal oxide nanocrystals efficiently and economically.

SUMMARY

Embodiments relate to methods of metal oxide nanocrystals preparation. According to embodiments, a metal-organic precursor may be economically synthesized by reacting a metal with an organic acid, which contains an aliphatic chain longer than three carbon atoms. The metal may be In, Sn, Al, Ga, Zn, Cd, Sb, Bi, Ge, Mn, Ti, Nb, V, Cr, Mo, Fe, Y, Mg, Co, and mixtures thereof. Further processing of the metal-organic precursor (e.g. by pyrolysis, hydrolysis, or alcoholysis) produces metal oxide nanocrystals of desired characteristics. A metal-organic precursor of indium tin oxide (ITO) may be synthesized by reacting indium metal and tin metal with an organic acid having an aliphatic chain longer than three carbon atoms (e.g. stearic acid) at a temperature above 200° C. Further processing of the resulting metal-organic precursor yields ITO nanocrystals of regular shape, uniform size, and average diameter ranging of between about 1 nm to 500 nm.

DETAILED DESCRIPTION

Embodiments relate to methods of metal oxide nanocrystals preparation. According to some embodiments, a metal-organic precursor may be economically synthesized by reacting a metal with an organic acid, which includes an aliphatic chain longer than three carbon atoms. The metal may be selected from the group consisting of In, Sn, Al, Ga, Zn, Cd, Sb, Bi, Ge, Mn, Ti, Nb, V, Cr, Mo, Fe, Y, Mg, Co, and mixtures thereof. Further processing of the metal-organic precursor (e.g. by pyrolysis, hydrolysis, or alcoholysis) produces metal oxide nanocrystals of desired characteristics. In some embodiments, without adding organic solvent or surfactant, metal oxide nanocrystals could be prepared by directly pyrolyzing the as-synthesized metal-organic precursor. A metal-organic precursor of indium tin oxide (ITO) may be synthesized by reacting indium metal and tin metal with an organic acid having an aliphatic chain longer than three carbon atoms (e.g. stearic acid) at a temperature above 200° C. Further processing of the resulting metal-organic precursor yields ITO nanocrystals of regular shape, uniform size, and average diameter ranging of between about 1 nm to 500 nm.

Figure 1:
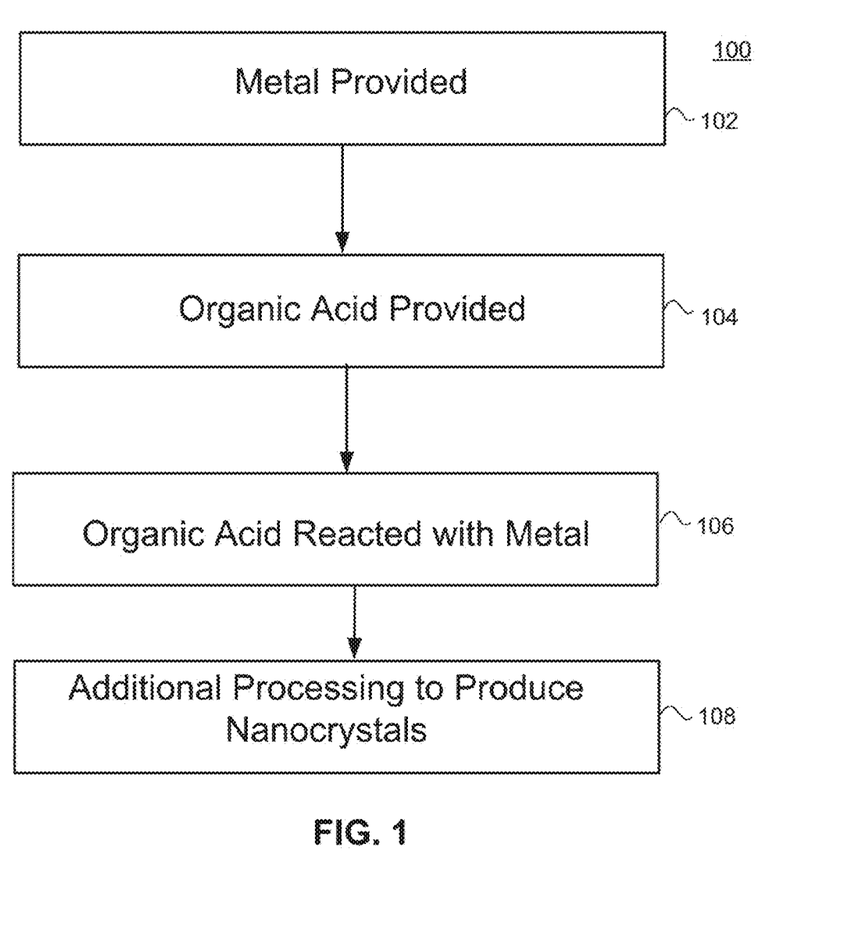
FIG. 1 is a simplified flow diagram showing a method of forming a TCO according to an embodiment.

FIG. 1 is a simplified flow diagram showing a method 100 of forming a TCO according to an embodiment. In a first step 102 a metal is provided.

The metal may comprise an element selected from the group consisting of In, Sn, Al, Ga, Zn, Cd, Sb, Bi, Ge, Mn, Ti, Nb, V, Cr, Mo, Fe, Y, Mg, and Co. Mixtures of metals may be used. One example of a metal is indium, which together with tin metal forms ITO.

One type of TCOs is unary metal oxide, such as $SnO_2$, ZnO, $Ga_2O_3$ and CdO. Another type of TCO is doped metal oxide, such as ITO (Indium tin oxide), IZO (Indium zinc oxide), AZO (Aluminum zinc oxide), ATO (Antimony tin oxide), GZO (Gallium zinc oxide) and FTO (Fluorine-doped tin oxide).

Binary metal oxide is another type of TCO. Typical materials are $ZnO$—$SnO_2$, $ZnO$—$In_2O_3$, $In_2O_3$—$SnO_2$, $CdO$—$SnO_2$, $CdO$—$In_2O_3$, $GaInO_3$, $(Ga, In)_2O_3$, $CdSb_2O_6$ and $MgIn_2O_4$.

Some ternary metal oxides and quaternary metal oxides may be used as TCOs. Examples include but are not limited to $Zn$—$In_2O_3$—$SnO_2$, $CdO$—$In2O_3$—$SnO_2$, $ZnO$—$CdO$—$In_2O_3$—$SnO_2$ and IGZO (Indium gallium zinc oxide).

Returning to the process flow of FIG. 1, in a second step 104 an organic acid is provided. In certain embodiments this organic acid includes an aliphatic chain longer than three carbon atoms. Types of organic acids which may be used in the reaction may comprise fatty acids, carboxylic acids, aromatic acids, sulfonic acid, or mixtures thereof.

According to certain embodiments, fatty acids having aliphatic chains of three (3) carbon atoms or longer may be used. One specific example is stearic acid, a fatty acid having an aliphatic tail comprising sixteen (16) carbon atoms.

Fatty acids may exist in saturated form. The following table comprises a list of saturated fatty acids.

| Common Name | Systematic Name | Structural Formula | Lipid Numbers |
|---|---|---|---|
| Propionic acid | Propanoic acid | $CH_3CH_2COOH$ | C3:0 |
| Butyric acid | Butanoic acid | $CH_3(CH_2)_2COOH$ | C4:0 |
| Valeric acid | Pentanoic acid | $CH_3(CH_2)_3COOH$ | C5:0 |
| Caproic acid | Hexanoic acid | $CH_3(CH_2)_4COOH$ | C6:0 |
| Enanthic acid | Heptanoic acid | $CH_3(CH_2)_5COOH$ | C7:0 |
| Caprylic acid | Octanoic acid | $CH_3(CH_2)_6COOH$ | C8:0 |
| Pelargonic acid | Nonanoic acid | $CH_3(CH_2)_7COOH$ | C9:0 |
| Capric acid | Decanoic acid | $CH_3(CH_2)_8COOH$ | C10:0 |
| Undecylic acid | Undecanoic acid | $CH_3(CH_2)_9COOH$ | C11:0 |
| Lauric acid | Dodecanoic acid | $CH_3(CH_2)_{10}COOH$ | C12:0 |
| Tridecylic acid | Tridecanoic acid | $CH_3(CH_2)_{11}COOH$ | C13:0 |
| Myristic acid | Tetradecanoic acid | $CH_3(CH_2)_{12}COOH$ | C14:0 |
| Pentadecylic acid | Pentadecanoic acid | $CH_3(CH_2)_{13}COOH$ | C15:0 |
| Palmitic acid | Hexadecanoic acid | $CH_3(CH_2)_{14}COOH$ | C16:0 |
| Margaric acid | Heptadecanoic acid | $CH_3(CH_2)_{15}COOH$ | C17:0 |
| Stearic acid | Octadecanoic acid | $CH_3(CH_2)_{16}COOH$ | C18:0 |
| Nonadecylic acid | Nonadecanoic acid | $CH_3(CH_2)_{17}COOH$ | C19:0 |
| Arachidic acid | Eicosanoic acid | $CH_3(CH_2)_{18}COOH$ | C20:0 |
| Heneicosylic acid | Heneicosanoic acid | $CH_3(CH_2)_{19}COOH$ | C21:0 |
| Behenic acid | Docosanoic acid | $CH_3(CH_2)_{20}COOH$ | C22:0 |
| Tricosylic acid | Tricosanoic acid | $CH_3(CH_2)_{21}COOH$ | C23:0 |
| Lignoceric acid | Tetracosanoic acid | $CH_3(CH_2)_{22}COOH$ | C24:0 |
| Pentacosylic acid | Pentacosanoic acid | $CH_3(CH_2)_{23}COOH$ | C25:0 |
| Cerotic acid | Hexacosanoic acid | $CH_3(CH_2)_{24}COOH$ | C26:0 |
| Heptacosylic acid | Heptacosanoic acid | $CH_3(CH_2)_{25}COOH$ | C27:0 |
| Montanic acid | Octacosanoic acid | $CH_3(CH_2)_{26}COOH$ | C28:0 |
| Nonacosylic acid | Nonacosanoic acid | $CH_3(CH_2)_{27}COOH$ | C29:0 |
| Melissic acid | Triacontanoic acid | $CH_3(CH_2)_{28}COOH$ | C30:0 |
| Henatriacontylic acid | Henatriacontanoic acid | $CH_3(CH_2)_{29}COOH$ | C31:0 |
| Lacceroic acid | Dotriacontanoic acid | $CH_3(CH_2)_{30}COOH$ | C32:0 |
| Psyllic acid | Tritriacontanoic acid | $CH_3(CH_2)_{31}COOH$ | C33:0 |
| Geddic acid | Tetratriacontanoic acid | $CH_3(CH_2)_{32}COOH$ | C34:0 |
| Ceroplastic acid | Pentatriacontanoic acid | $CH_3(CH_2)_{33}COOH$ | C35:0 |
| Hexatriacontylic acid | Hexatriacontanoic acid | $CH_3(CH_2)_{34}COOH$ | C36:0 |

Fatty acids may exist in unsaturated form. The following table comprises a list of unsaturated fatty acids.

| Common name | Chemical structure | $\Delta^x$ | C:D | n-x |
|---|---|---|---|---|
| Myristoleic acid | $CH_3(CH_2)_3CH=CH(CH_2)_7COOH$ | cis-$\Delta^9$ | 14:1 | n-5 |
| Palmitoleic acid | $CH_3(CH_2)_5CH=CH(CH_2)_7COOH$ | cis-$\Delta^9$ | 16:1 | n-7 |
| Sapienic acid | $CH_3(CH_2)_8CH=CH(CH_2)_4COOH$ | cis-$\Delta^6$ | 16:1 | n-10 |
| Oleic acid | $CH_3(CH_2)_7CH=CH(CH_2)_7COOH$ | cis-$\Delta^9$ | 18:1 | n-9 |
| Elaidic acid | $CH_3(CH_2)_7CH=CH(CH_2)_7COOH$ | trans-$\Delta^9$ | 18:1 | n-9 |
| Vaccenic acid | $CH_3(CH_2)_5CH=CH(CH_2)_9COOH$ | trans-$\Delta^{11}$ | 18:1 | n-7 |
| Linoleic acid | $CH_3(CH_2)_4CH=CHCH_2CH=CH(CH_2)_7COOH$ | cis,cis-$\Delta^9,\Delta^{12}$ | 18:2 | n-6 |
| Linoelaidic acid | $CH_3(CH_2)_4CH=CHCH_2CH=CH(CH_2)_7COOH$ | trans,trans-$\Delta^9,\Delta^{12}$ | 18:2 | n-6 |
| α-Linolenic acid | $CH_3CH_2CH=CHCH_2CH=CHCH_2CH=CH(CH_2)_7COOH$ | cis,cis,cis-$\Delta^9,\Delta^{12},\Delta^{15}$ | 18:3 | n-3 |
| Arachidonic acid | $CH_3(CH_2)_4CH=CHCH_2CH=CHCH_2CH=CHCH_2CH=CH(CH_2)_3COOH$ | cis,cis,cis,cis-$\Delta^5,\Delta^8,\Delta^{11},\Delta^{14}$ | 20:4 | n-6 |
| Eicosapentaenoic acid | $CH_3CH_2CH=CHCH_2CH=CHCH_2CH=CHCH_2$ $CH=CHCH_2CH=CH(CH_2)_3COOH$ | cis,cis,cis,cis,cis-$\Delta^5,\Delta^8,\Delta^{11},\Delta^{14},\Delta^{17}$ | 20:5 | n-3 |
| Erucic acid | $CH_3(CH_2)_7CH=CH(CH_2)_{11}COOH$ | cis-$\Delta^{13}$ | 22:1 | n-9 |
| Docosahexaenoic acid | $CH_3CH_2CH=CHCH_2CH=CHCH_2CH=CHCH_2$ $CH=CHCH_2CH=CHCH_2CH=CH(CH_2)_2COOH$ | cis,cis,cis,cis,cis,cis-$\Delta^4,\Delta^7,\Delta^{10},\Delta^{13},\Delta^{16},\Delta^{19}$ | 22:6 | n-3 |

The following table comprises a list of Omega-3 fatty acids, polyunsaturated.

| Common name | Lipid name | Chemical name |
|---|---|---|
| Hexadecatrienoic acid (HTA) | 16:3 (n-3) | all-cis 7,10,13-hexadecatrienoic acid |
| Alpha-linolenic acid (ALA) | 18:3 (n-3) | all-cis-9,12,15-octadecatrienoic acid |
| Stearidonic acid (SDA) | 18:4 (n-3) | all-cis-6,9,12,15,-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA, Timnodonic acid) | 20:5 (n-3) | all-cis-5,8,11,14,17-eicosapentaenoic acid |

-continued

| Common name | Lipid name | Chemical name |
|---|---|---|
| Heneicosapentaenoic acid (HPA) | 21:5 (n-3) | all-cis-6,9,12,15,18-heneicosapentaenoic acid |
| Docosapentaenoic acid (DPA, Clupanodonic acid) | 22:5 (n-3) | all-cis-7,10,13,16,19-docosapentaenoic acid |
| Docosahexaenoic acid (DHA, Cervonic acid) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |

The following table comprises a list of Omega-6 fatty acids, polyunsaturated.

| Common name | Lipid name | Chemical name |
|---|---|---|
| Linoleic acid | 18:2 (n-6) | all-cis-9,12-octadecadienoic acid |
| Gamma-linolenic acid (GLA) | 18:3 (n-6) | all-cis-6,9,12-octadecatrienoic acid |
| Eicosadienoic acid | 20:2 (n-6) | all-cis-11,14-eicosadienoic acid |
| Dihomo-gamma-linolenic acid (DGLA) | 20:3 (n-6) | all-cis-8,11,14-eicosatrienoic acid |
| Arachidonic acid (AA) | 20:4 (n-6) | all-cis-5,8,11,14-eicosatetraenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid (Osbond acid) | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |

The following table comprises a list of Omega-9 fatty acids, mono- and polyunsaturated

| Common name | Lipid name | Chemical name |
|---|---|---|
| Oleic acid[†] | 18:1 (n-9) | cis-9-octadecenoic acid |
| Eicosenoic acid[†] | 20:1 (n-9) | cis-11-eicosenoic acid |
| Mead acid | 20:3 (n-9) | all-cis-5,8,11-eicosatrienoic acid |
| Erucic acid[†] | 22:1 (n-9) | cis-13-docosenoic acid |
| Nervonic acid[†] | 24:1 (n-9) | cis-15-tetracosenoic acid |

[†]Monounsaturated

Conjugated fatty acids have two or more conjugated double bonds. A table of certain such fatty acids is provided below.

| Common name | Lipid name | Chemical name |
|---|---|---|
| Conjugated Linoleic Acids (two conjugated double bonds) | | |
| Rumenic acid | 18:2 (n-7) | 9Z,11E-octadeca-9,11-dienoic acid |
| | 18:2 (n-6) | 10E,12Z-octadeca-9,11-dienoic acid |
| Conjugated Linolenic Acids (three conjugated double bonds) | | |
| α-Calendic acid | 18:3 (n-6) | 8E,10E,12Z-octadecatrienoic acid |
| β-Calendic acid | 18:3 (n-6) | 8E,10E,12E-octadecatrienoic acid |
| Jacaric acid | 18:3 (n-6) | 8Z,10E,12Z-octadecatrienoic acid |
| α-Eleostearic acid | 18:3 (n-5) | 9Z,11E,13E-octadeca-9,11,13-trienoic acid |
| β-Eleostearic acid | 18:3 (n-5) | 9E,11E,13E-octadeca-9,11,13-trienoic acid |
| Catalpic acid | 18:3 (n-5) | 9Z,11Z,13E-octadeca-9,11,13-trienoic acid |
| Punicic acid | 18:3 (n-5) | 9Z,11E,13Z-octadeca-9,11,13-trienoic acid |
| Other | | |
| Rumelenic acid | 18:3 (n-3) | 9E,11Z,15E-octadeca-9,11,15-trienoic acid |
| α-Parinaric acid | 18:4 (n-3) | 9E,11Z,13Z,15E-octadeca-9,11,13-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |

A sulfonic acid has the general formula $RS(=O)_2-OH$, where R is an organic alkyl or aryl group. Perfluorooctanesulfonic acid and dodecylbenzenesulfonic acid are particular representative examples of sulfonic acids, which could be used in the method to react with a metal.

Returning to FIG. 1, in a third step 106 the organic acid and the metal are mixed together and heated to a temperature at or higher than a reacting point, at which the organic acid begins to react with the metal. The temperature may depend upon the relative reactivity of the metal and the organic acid. In certain embodiments the heating may be to a temperature of about 100° C., about 125° C., about 150° C., about 175° C., about 200° C., about 225° C., about 250° C., about 275° C., about 300° C., about 325° C., about 350° C., about 375° C., about 400° C., or higher.

In certain embodiments this mixing occurs neat, without the presence of other organic solvent. This heating may take place in an atmosphere of nitrogen or other than nitrogen (e.g., air), and may take place at atmospheric pressure or higher. During this step 106, the metal and the organic acid react to form a metal-organic complex. The heating can last for a period of time until the reaction has completed. Hydrogen may be released during reaction.

In a fourth step 108, the metal-organic precursor is subjected to additional processing to form a TCO particle having the desired size. In certain embodiments this additional processing may comprise precipitation. Additional processing may comprise exposure to heat (pyrolysis), exposure to water (hydrolysis), and/or exposure to alcohol (alcoholysis).

Where pyrolysis is used, the heating may be to a temperature of about 150° C., about 200° C., about 250° C., about 300° C., about 350° C., about 400° C., about 450° C., or higher.

Where hydrolysis is used, the heating may be to a temperature of about 100° C., about 150° C., about 200° C., about 250° C., about 300° C., about 350° C., or higher, followed by calcination of hydrolysates at a high temperature of about 400° C., about 500° C., about 600° C., about 700° C., about 800° C., or about 900° C., or higher.

Where alcoholysis is used, the heating may be to a temperature of about 100° C., about 150° C., about 200° C., about 250° C., or about 300° C., about 350° C., or higher.

Nanocrystals of TCO material resulting from the additional processing, may have an average diameter of about 1 nm, about 2 nm, about 5 nm, about 10 nm, about 15 nm, about 20 nm, about 25 nm, about 30 nm, about 40 nm, about 50 nm, about 100 nm, or about 200 nm.

Although not shown in FIG. 1, further processing is possible. In particular, a TCO material formed according to embodiments may next be formed on the surface of a workpiece in conjunction with the fabrication of an electro-optic device (e.g. solar cell, LCD screen, touchscreen).

For example, a TCO material may be formed by fabrication steps such as sputtering, metal organic chemical vapor deposition (MOCVD), metal organic molecular beam deposition (MOMBD), spray pyrolysis, and/or pulsed laser deposition (PLD).

In connection with preparation of a TCO material for use in a sputtering process, a TCO material may be incorporated within a sputtering target. Desirable results may be obtained utilizing an ITO sputtering target having a high sintering density (above 98% of theoretical density). To produce such an ITO target utilizing ITO powder or $In_2O_3/SnO_2$ powder, the powders may be present in a suitable size with a narrow particle size distribution.

TCO films could be directly made by pyrolyzing as-synthesized metal-organic precursors. Another method to fabricate a TCO film is directly to deposit TCO particles on the substrate via a solution. The TCO nanocrystals in a suitable size with a narrow particle size distribution, would improve the performance of the TCO film.

Examples of preparation of a TCO material in the form of indium tin oxide (ITO), are now described. Specifically, an indium organic compound and a tin organic compound are synthesized by reacting an organic acid with indium metal, tin metal, or a mixture of indium metal and tin metal.

In this example, stearic acid ($CH_3(CH_2)_{16}CO_2H$) a fatty acid comprising an aliphatic tail of sixteen (16) carbon atoms, is used as the organic acid. Stearic acid has a boiling point of 376° C., well above the reacting points of both indium and tin.

It is further noted that different organic acids could be reacted with indium metal or tin metal. However, in this particular embodiment the same organic acid (e.g., stearic acid), is used.

Following creation of the organic precursors, ITO nanocrystals could be prepared via various routes using the as-synthesized indium organic compound and tin organic compound.

One route to synthesis of ITO nanocrystals is by pyrolysis. There, ITO nanocrystals are synthesized by decomposing the mixture containing indium organic compound and tin organic compound at a temperature above their decomposition points.

A second route to synthesis of ITO nanocrystals is by hydrolysis. There, ITO nanocrystals are prepared by hydrolyzing the mixture containing indium organic compound and tin organic compound at a certain temperature to obtain hydrolysates. The hydrolysates are then calcined to obtain indium tin oxide.

In an example, the indium organic compound, the tin organic compound, and water are added to a sealed reactor under a pressure above 1 atm and at a temperature of about 100-350° C. In certain embodiments the temperature may be about 120° C.

The as-synthesized hydrolysates are then calcined at a high temperature of about 400-1000° C. In certain embodiments the temperature may be about 600° C.

A third route to synthesis of ITO nanocrystals is by alcoholysis. There, ITO nanocrystals are prepared by alcoholyzing the mixture containing indium organic compound and tin organic compound.

Alcoholysis can be carried out under solvothermal conditions where indium organic compound, tin organic compound, and alcohol are put together in a sealed reactor under a pressure above 1 atm and at a temperature above the boiling point of the selected alcohol. A variety of alcohols may be used, including but not limited to methanol, ethanol, propanol, butanol, and amyl alcohol. In a particular embodiment, ethanol may be used.

According to embodiments, ITO nanoparticles having regular shapes, uniform size and an average size of between about 1-500 nm can be synthesized by pyrolysis. ITO nanoparticles having an average size of between about 5-500 nm can be synthesized by hydrolysis following calcination. ITO nanoparticles having uniform size and an average size of between about 1-500 nm can be synthesized by alcoholysis.

Several examples of embodiments synthesizing ITO under a variety of different conditions, are now provided below for further illustration.

EXAMPLE 1

In a first example, 0.11 g tin metal, 1.00 g indium metal, and 10 g stearic acid were put in a reactor. The reactor could be a flask or other container.

The mixture was heated with stirring at 340° C. for 15 minutes in a nitrogen atmosphere. A wax mixture containing tin stearate and indium stearate was formed.

EXAMPLE 2

In this second example, 0.21 g tin metal, 2.00 g indium metal, and 10 g stearic acid were put in a reactor. The mixture was heated with stirring at 330° C. for half an hour in a nitrogen atmosphere.

During the heating, tin stearate and indium stearate were formed and then decomposed. A blue precipitate was obtained. The blue mixture was aged for 7 hours at 330° C., and then cooled to room temperature.

Chloroform was used to wash the blue mixture. After washing and centrifugation for several times, a blue powder was finally obtained.

Figure 2:
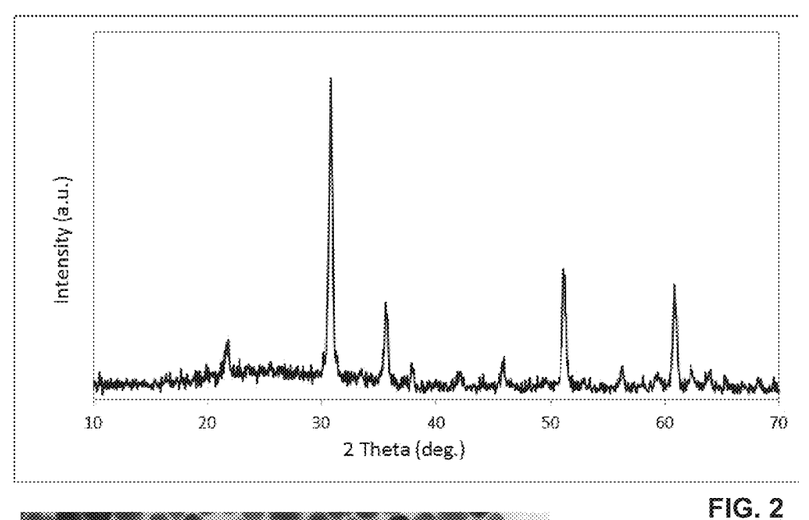
FIG. 2 is an X-ray powder diffraction (XRD) pattern of the blue product from the Example 2.

The X-ray diffraction (XRD) pattern of the blue powder (FIG. 2) showed $In_2O_3$ peaks, with no $SnO_2$ peaks being apparent. This indicated formation of indium tin oxide.

Figure 3:
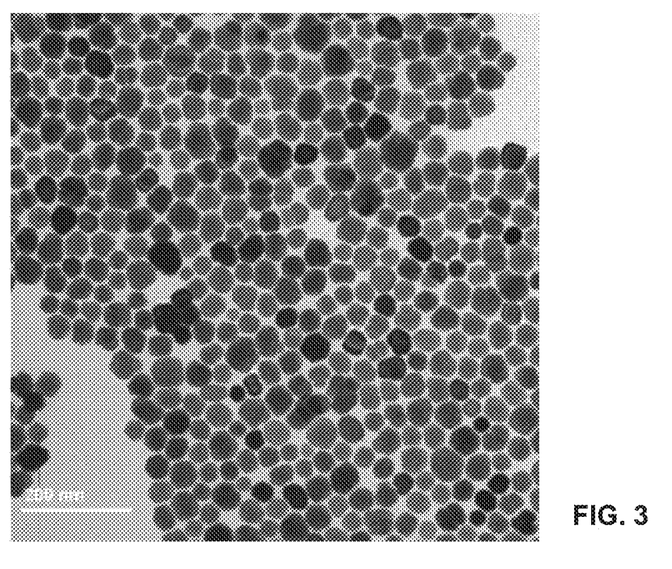
FIG. 3 is a transmission electron microscopy (TEM) image of the blue product from the Example 2.

The transmission electron microscopy (TEM) image of the blue powder (FIG. 3) showed that the ITO particles possessed regular shapes and uniform size, with size distribution between about 30 nm and 50 nm. The average particle size of the ITO nanocrystals was about 40 nm.

EXAMPLE 3

In this third example, 0.21 g tin metal, 2.00 g indium metal, and 10 g stearic acid were put in a reactor. The mixture was heated with stirring at 260° C. for 4 hours in a nitrogen atmosphere, and then cooled to room temperature.

Chloroform was used to wash the blue mixture. After washing and centrifugation for several times, a blue powder was finally obtained.

Figure 4:
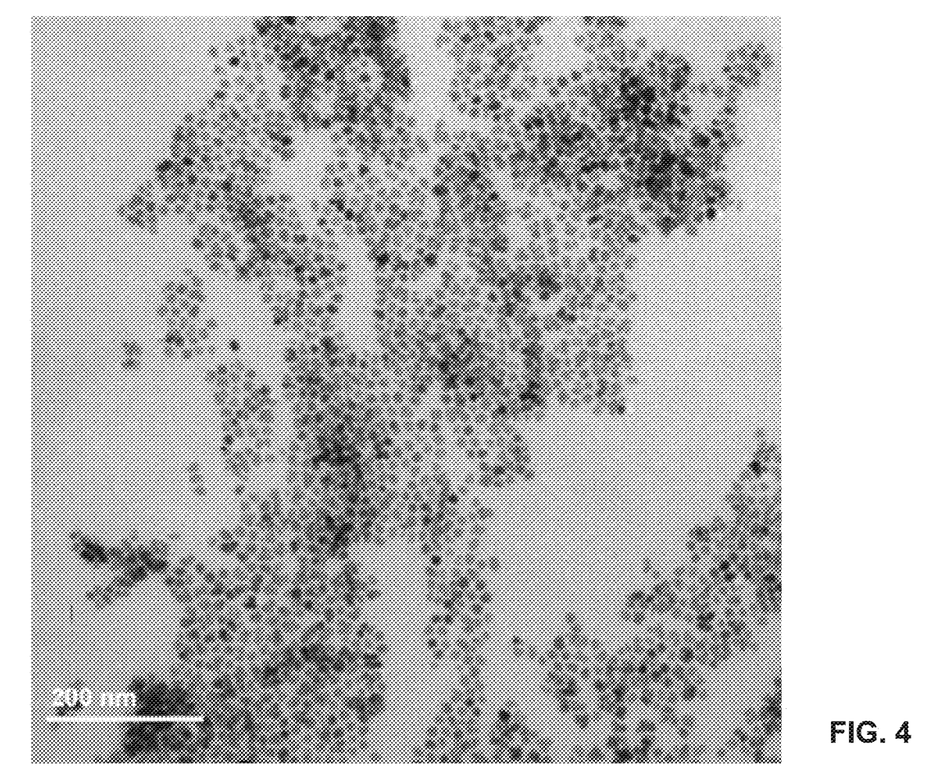
FIG. 4 is the TEM image of the blue product from the Example 3.

FIG. 4 shows the TEM image of the blue product. This TEM image indicates that the nanocrystals were at average size of ~10 nm with a size distribution between 5 nm and 15 nm.

EXAMPLE 4

In this fourth example, 5.00 g wax product from the Example 1, and 1 g de-ionized water were put in a 100 mL autoclave, and heated at 110° C. for 19 hours after proper sealing. The mixture was then cooled to room temperature.

Chloroform was used to wash the mixture. After washing and centrifugation for several times, a white intermediate product was obtained.

Figure 5:
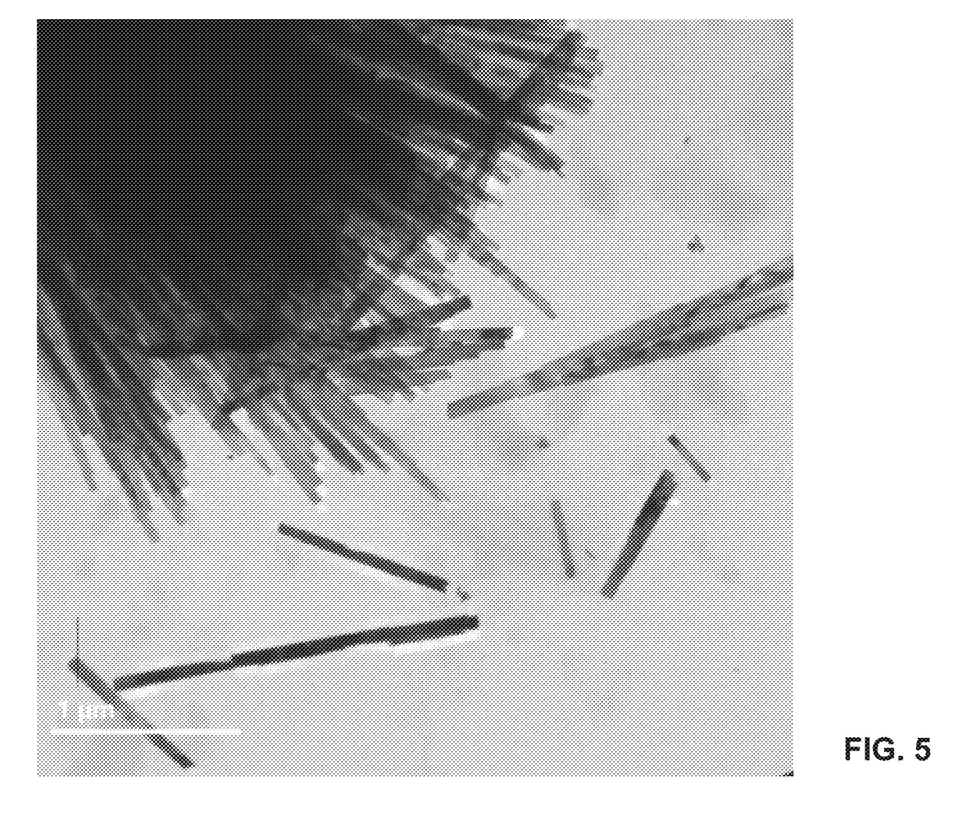
FIG. 5 is the TEM image of the white intermediate product from the Example 4.
Figure 6:
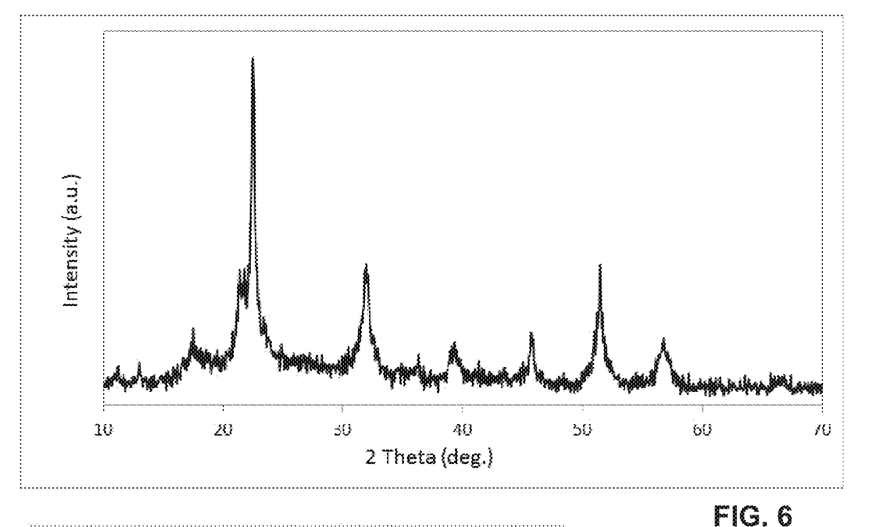
FIG. 6 is the XRD pattern of the white intermediate product from the Example 4.

The TEM image (FIG. 5) of the white intermediate products showed that nanofibers were obtained. The XRD pattern (FIG. 6) showed that the white intermediate products were hydroxides.

Figure 7:
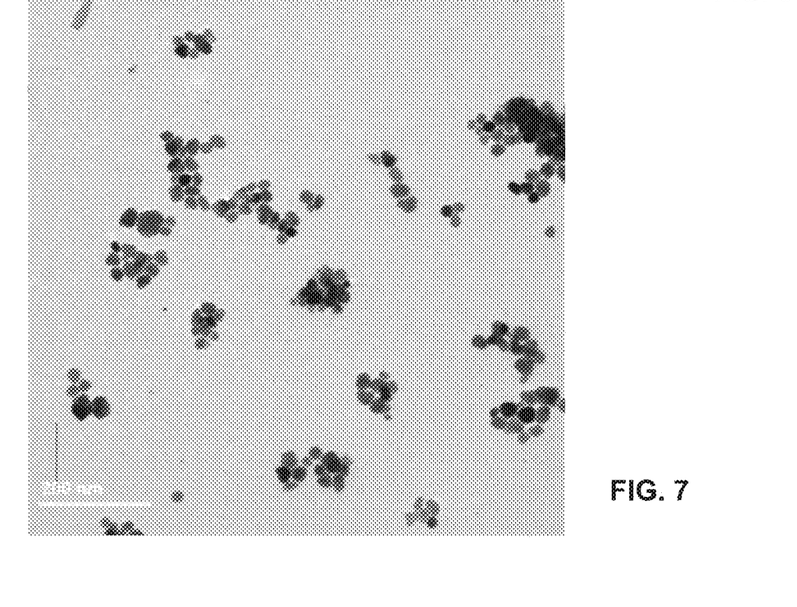
FIG. 7 is the TEM image of the yellow product after calcination from Example 4.

A yellow final product can be prepared by calcining the white intermediate product at 600° C. for 2 hours. The TEM image (FIG. 7) of the yellow final product revealed that the particles have a size distribution between 15 nm and 30 nm.

EXAMPLE 5

Here 3 g wax product from the Example 1, and 10 g 1-amyl alcohol were put in a 100 mL autoclave, and heated at 250° C. for 6 hours after proper sealing. After reaction, a blue product was obtained.

Figure 8:
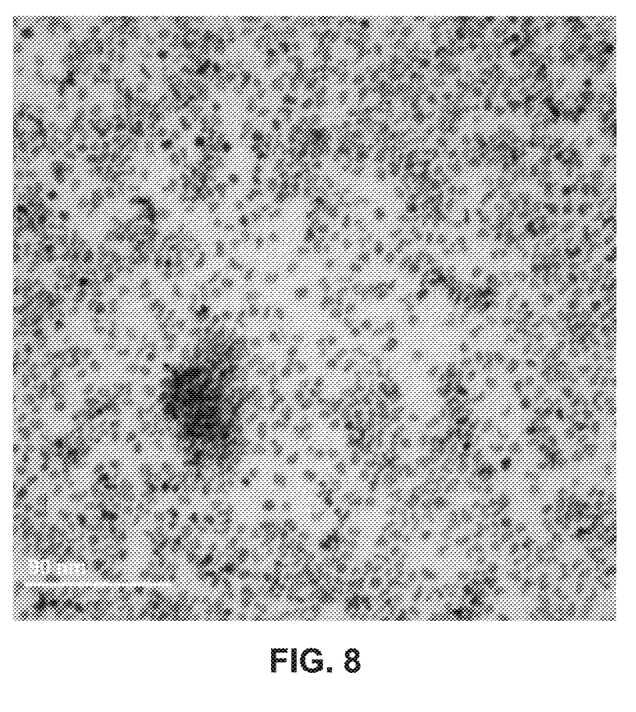
FIG. 8 is the TEM image of the blue product from the Example 5.

The TEM image of the blue product is shown in FIG. 8. This TEM image indicates the ITO nanocrystals to be of average size of ~5 nm, with a size distribution between about 3-7 nm.

EXAMPLE 6

In this sixth example, 1.00 g tin metal and 5 g stearic acid were put in a reactor. The mixture was heated with stirring at 330° C. for half an hour in a nitrogen atmosphere. 0.15 g tin was dissolved and organic mixture A was obtained.

Next, 1.50 g indium metal and 11.2 g stearic acid were put in a reactor. The mixture was heated with stiffing at 260° C. for 6 hours in a nitrogen atmosphere. Indium metal was completely dissolved and organic mixture B was obtained.

Mixture A and mixture B were then placed in a reactor and were heated with stirring at 300° C. for 4 hours in a nitrogen atmosphere. A blue precipitate was obtained. The blue product comprised ITO nanocrystals with an average size of about 30 nm.

EXAMPLE 7

In this seventh example, 0.1 g tin metal, 1.00 g indium metal, and 16.4 g stearic acid were put into a reactor. The mixture was heated with stirring at 300° C. for 40 minutes in a nitrogen atmosphere. Then the temperature was increased to 320° C. and maintained for 4.5 hours.

Figure 9:
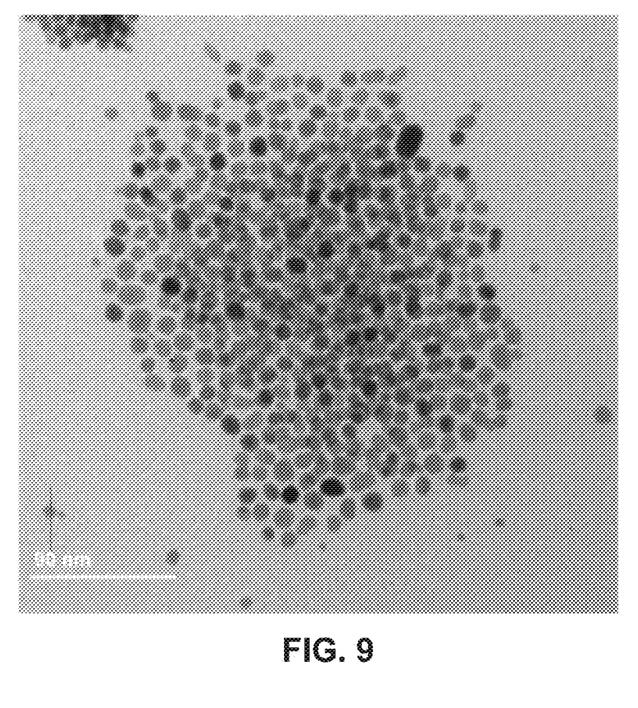
FIG. 9 is the TEM image of the blue product from the Example 7.

The blue precipitates were obtained and purified by chloroform. The TEM image (FIG. 9) of the final product showed that the ITO nanocrystals were at average size of ~10 nm.

EXAMPLE 8

In this eighth example, 6.57 g zinc metal and 28.4 g stearic acid were put into a reactor. The mixture was heated with stirring in a nitrogen atmosphere. Zinc began to react with stearic acid when the temperature was above 150° C. The reaction become vigorous after the temperature increased to 250° C. Zinc stearate was obtained after the reaction was completed.

EXAMPLE 9

In this ninth example, 2.36 g gallium metal and 28.4 g stearic acid were put into a reactor. The mixture was heated with stirring in a nitrogen atmosphere. Gallium reacted vigorously with stearic acid at 250° C. Large amount of gases were produced during the reaction. Gallium stearate was obtained after reaction was completed.

EXAMPLE 10

In this tenth example, 5.6 g of iron (Fe) powder and 28.4 g stearic acid were put into a reactor. The mixture was heated with stirring in a nitrogen atmosphere. Iron reacted vigorously with stearic acid at 250° C. Large amount of gases were produced during the reaction. Iron stearate was obtained after reaction was completed.

Each of the following documents is incorporated by reference in its entirety herein for all purposes:
1. Lee J., Lee S., Li G., Petruska M. A., Paine D. C. and Sun S., A facile solution-phase approach to transparent and conducting ITO nanocrystal assemblies, Journal of the American Chemical Society, 2012, 134:p. 13410-13414.
2. Park J., Joo J., Kwon S. G., Jang Y. and Hyeon T., Synthesis of monodisperse spherical nanocrystals, Angewandte Chemie International Edition, 2007. 46: p. 4630-60.
3. Kanehara M., Koike H., Yoshinaga T. and Teranishi T., Indium tin oxide nanoparticles with compositionally tunable surface plasmon resonance frequencies in the near-IR region, Journal of the American Chemical Society, 2009, 131 (49): p. 17736-17737.

What is claimed is:
1. A method comprising:
   forming a first metal-organic precursor by conducting a neat reaction of a first metal with an organic acid at a first temperature at or higher than a reacting point at which the organic acid begins to react with the first metal, wherein the organic acid comprises a carboxylic fatty acid having three or more carbon atoms; and
   performing additional processing to convert the first metal-organic precursor to metal oxide nanocrystals, wherein the additional processing comprises hydrolysis following further calcination.

2. A method as in claim 1 wherein the organic acid comprises an aliphatic chain longer than three carbon atoms.

3. A method as in claim 1 wherein the first metal is selected from the group consisting of In, Sn, Al, Ga, Zn, Cd, Sb, Bi, Ge, Mn, Ti, Nb, V, Cr, Mo, Fe, Y, Mg, and Co.

4. A method as in claim 1 wherein the first metal comprises tin.

5. A method as in claim 1 wherein the first metal comprises indium.

6. A method as in claim 1 further comprising forming a second metal-organic precursor from reaction between a second metal and the organic acid.

7. A method as in claim 6 wherein the first metal comprises indium, the second metal comprises tin, and the organic acid comprises an aliphatic chain longer than three carbon atoms.

8. A method as in claim 6 further comprising forming a third metal-organic precursor from reaction between a third metal and the organic acid.

9. A method as in claim 1 wherein the organic acid comprises a fatty acid with an aliphatic chain of more than six carbon atoms.

10. A method as in claim 9 wherein the fatty acid comprises stearic acid.

11. A method comprising:
forming a first metal-organic precursor by conducting a neat reaction of a first metal with an organic acid at a first temperature at or higher than a reacting point at which the organic acid begins to react with the first metal, wherein the organic acid comprises a carboxylic fatty acid having three or more carbon atoms; and
performing additional processing to convert the first metal-organic precursor to metal oxide nanocrystals, wherein the additional processing comprises the addition of alcohol to cause alcoholysis.

12. A method as in claim 1 wherein the nanocrystals have sizes between about 1-500 nm.

13. A method as in claim 1 wherein the first temperature is between about 100-400° C.

14. A method as in claim 1 wherein the neat reaction is performed in a nitrogen atmosphere.

15. A method as in claim 1 wherein the neat reaction is performed at greater than atmospheric pressure.

16. A method as in claim 11 wherein the organic acid comprises an aliphatic chain longer than three carbon atoms.

17. A method as in claim 11 wherein the first metal comprises tin, indium, iron, zinc, gallium, cobalt, or manganese.

18. A method as in claim 11 wherein the nanocrystals have sizes between about 5-300 nm.

19. A method as in claim 11 wherein the first temperature is between about 100-400° C.

20. A method as in claim 11 wherein the neat reaction is performed in a nitrogen atmosphere.

* * * * *